(12) United States Patent
Lab et al.

(10) Patent No.: US 8,197,517 B1
(45) Date of Patent: Jun. 12, 2012

(54) FRICTIONAL POLYAXIAL SCREW ASSEMBLY

(75) Inventors: Eric A. Lab, Wadsworth, OH (US);
Peter A. Materna, Metuchen, NJ (US)

(73) Assignee: Theken Spine, LLC, Akron, OH (US)

( * ) Notice: Subject to any disclaimer, the term of this patent is extended or adjusted under 35 U.S.C. 154(b) by 956 days.

(21) Appl. No.: 12/117,613

(22) Filed: May 8, 2008

Related U.S. Application Data

(60) Provisional application No. 60/916,659, filed on May 8, 2007, provisional application No. 60/939,977, filed on May 24, 2007.

(51) Int. Cl.
*A61B 17/70* (2006.01)
(52) U.S. Cl. ...................................... 606/268
(58) Field of Classification Search .......... 606/265–272, 606/279
See application file for complete search history.

(56) References Cited

U.S. PATENT DOCUMENTS

| | | | |
|---|---|---|---|
| 2,699,774 A | 1/1955 | Livingston |
| 4,653,481 A | 3/1987 | Howland et al. |
| 4,719,905 A | 1/1988 | Steffee |
| 4,805,602 A | 2/1989 | Puno et al. |
| 4,950,269 A | 8/1990 | Gaines, Jr. |
| 5,053,036 A | 10/1991 | Perren et al. |
| 5,085,660 A | 2/1992 | Lin |
| 5,108,395 A | 4/1992 | Laurain |
| 5,112,332 A | 5/1992 | Cozad et al. |
| 5,116,334 A | 5/1992 | Cozad et al. |
| 5,152,303 A | 10/1992 | Allen |
| 5,154,719 A | 10/1992 | Cotrel |
| 5,181,917 A | 1/1993 | Rogozinski |
| 5,196,013 A | 3/1993 | Harms et al. |
| 5,207,678 A | 5/1993 | Harms et al. |
| 5,261,911 A | 11/1993 | Carl |
| 5,281,223 A | 1/1994 | Ray |
| 5,324,290 A | 6/1994 | Zdeblick et al. |
| 5,330,473 A | 7/1994 | Howland |
| 5,380,325 A | 1/1995 | Lahille et al. |

(Continued)

FOREIGN PATENT DOCUMENTS

WO   WO-0019923   4/2000

(Continued)

OTHER PUBLICATIONS

PCT/US2004/010319 International Search Report—Jul. 22, 2004.

(Continued)

*Primary Examiner* — Anu Ramana
(74) *Attorney, Agent, or Firm* — Middleton Reutlinger; Robert H. Eichenberger; Chad D. Bruggeman

(57) ABSTRACT

Various embodiments are provided with a polyaxial spinal screw assembly that comprise a threaded screw having a bulbous or curvate head, and a receiver for receiving the head of the screw, and a slotted collet between the receiver and the screw head. The collet may, in an un-locked condition, bear against the head of the screw to frictionally retain the screw's angular position. The collet may have a lip that may engage with a corresponding internal feature of the receiver. The screw head may be able to be inserted into the receiver through the bottom of the receiver. The screw may be cannulated and also may be fenestrated. Embodiments may also include a bone screw having fenestration holes that include a component in the rotational direction, such as backward-facing with respect to the forward-rotational direction of the screw.

6 Claims, 15 Drawing Sheets

U.S. PATENT DOCUMENTS

| | | | |
|---|---|---|---|
| 5,382,248 | A | 1/1995 | Jacobson et al. |
| 5,403,314 | A | 4/1995 | Currier |
| 5,443,467 | A | 8/1995 | Biedermann et al. |
| 5,466,237 | A | 11/1995 | Byrd, III et al. |
| 5,474,555 | A | 12/1995 | Puno et al. |
| 5,480,401 | A | 1/1996 | Navas |
| 5,486,176 | A | 1/1996 | Hildebrand et al. |
| 5,501,684 | A | 3/1996 | Schlapfer et al. |
| 5,549,608 | A | 8/1996 | Errico et al. |
| 5,554,157 | A | 9/1996 | Errico et al. |
| 5,584,834 | A | 12/1996 | Errico et al. |
| 5,586,984 | A | 12/1996 | Errico et al. |
| 5,591,165 | A | 1/1997 | Jackson |
| 5,591,235 | A | 1/1997 | Kuslich |
| 5,601,552 | A | 2/1997 | Cotrel |
| 5,615,965 | A | 4/1997 | Saurat et al. |
| 5,620,443 | A | 4/1997 | Gertzbein et al. |
| 5,624,442 | A | 4/1997 | Mellinger et al. |
| 5,669,911 | A | 9/1997 | Errico et al. |
| 5,672,176 | A | 9/1997 | Biedermann et al. |
| 5,681,319 | A * | 10/1997 | Biedermann et al. ......... 606/104 |
| 5,683,391 | A | 11/1997 | Boyd |
| 5,690,630 | A | 11/1997 | Errico et al. |
| 5,713,900 | A | 2/1998 | Benzel et al. |
| 5,716,356 | A | 2/1998 | Biedermann et al. |
| 5,725,527 | A | 3/1998 | Biedermann et al. |
| 5,728,098 | A | 3/1998 | Sherman et al. |
| 5,733,285 | A | 3/1998 | Errico et al. |
| 5,738,685 | A | 4/1998 | Halm et al. |
| 5,752,957 | A | 5/1998 | Ralph et al. |
| 5,782,833 | A | 7/1998 | Haider |
| 5,797,911 | A | 8/1998 | Sherman et al. |
| 5,800,435 | A | 9/1998 | Errico et al. |
| 5,817,094 | A | 10/1998 | Errico et al. |
| 5,863,293 | A | 1/1999 | Richelsoph |
| 5,879,350 | A | 3/1999 | Sherman et al. |
| 5,882,350 | A | 3/1999 | Ralph et al. |
| 5,885,286 | A | 3/1999 | Sherman et al. |
| 5,888,221 | A | 3/1999 | Gelbard |
| 5,891,145 | A | 4/1999 | Morrison et al. |
| 5,910,142 | A | 6/1999 | Tatar |
| 5,925,047 | A | 7/1999 | Errico et al. |
| 5,954,725 | A | 9/1999 | Sherman et al. |
| 5,964,760 | A | 10/1999 | Richelsoph |
| 5,989,254 | A | 11/1999 | Katz |
| 5,997,539 | A | 12/1999 | Errico et al. |
| 6,010,503 | A | 1/2000 | Richelsoph et al. |
| 6,017,344 | A | 1/2000 | Errico et al. |
| 6,019,759 | A | 2/2000 | Rogozinski |
| 6,022,350 | A | 2/2000 | Ganem |
| 6,048,343 | A | 4/2000 | Mathis et al. |
| 6,050,997 | A | 4/2000 | Mullane |
| 6,053,917 | A | 4/2000 | Sherman et al. |
| 6,063,090 | A | 5/2000 | Schlapfer |
| 6,074,391 | A | 6/2000 | Metz-Stavenhagen et al. |
| 6,090,111 | A | 7/2000 | Nichols |
| 6,113,601 | A | 9/2000 | Tatar |
| 6,132,430 | A | 10/2000 | Wagner |
| 6,132,432 | A | 10/2000 | Richelsoph |
| 6,132,434 | A | 10/2000 | Sherman et al. |
| 6,146,383 | A | 11/2000 | Studer et al. |
| 6,183,473 | B1 | 2/2001 | Ashman |
| 6,187,005 | B1 | 2/2001 | Brace et al. |
| 6,206,879 | B1 | 3/2001 | Marnay et al. |
| 6,210,376 | B1 | 4/2001 | Grayson |
| 6,214,006 | B1 | 4/2001 | Metz-Stavenhagen |
| RE37,161 | E | 5/2001 | Michelson et al. |
| 6,226,548 | B1 | 5/2001 | Foley et al. |
| 6,248,105 | B1 | 6/2001 | Schlapfer et al. |
| 6,254,602 | B1 | 7/2001 | Justis |
| 6,273,888 | B1 | 8/2001 | Justis |
| 6,280,442 | B1 | 8/2001 | Barker et al. |
| 6,280,443 | B1 | 8/2001 | Gu et al. |
| 6,287,311 | B1 | 9/2001 | Sherman et al. |
| 6,302,888 | B1 | 10/2001 | Mellinger et al. |
| 6,355,040 | B1 | 3/2002 | Richelsoph et al. |
| 6,361,535 | B2 | 3/2002 | Jackson |
| RE37,665 | E | 4/2002 | Ralph et al. |
| 6,368,321 | B1 | 4/2002 | Jackson |
| 6,371,957 | B1 | 4/2002 | Amrein et al. |
| 6,413,257 | B1 | 7/2002 | Lin et al. |
| 6,416,515 | B1 | 7/2002 | Wagner |
| 6,440,137 | B1 | 8/2002 | Horvath et al. |
| 6,454,768 | B1 | 9/2002 | Jackson |
| 6,454,773 | B1 | 9/2002 | Sherman et al. |
| 6,458,132 | B2 | 10/2002 | Choi |
| 6,471,705 | B1 | 10/2002 | Biedermann et al. |
| 6,475,218 | B2 | 11/2002 | Gournay et al. |
| 6,485,491 | B1 | 11/2002 | Farris et al. |
| 6,485,494 | B1 | 11/2002 | Haider |
| 6,488,681 | B2 | 12/2002 | Martin et al. |
| 6,537,276 | B2 | 3/2003 | Metz-Stavenhagen |
| 6,540,748 | B2 | 4/2003 | Lombardo |
| 6,547,790 | B2 | 4/2003 | Harkey, III et al. |
| 6,554,832 | B2 | 4/2003 | Shluzas |
| 6,554,834 | B1 | 4/2003 | Crozet et al. |
| 6,565,565 | B1 | 5/2003 | Yuan et al. |
| 6,565,567 | B1 | 5/2003 | Haider |
| 6,582,436 | B2 | 6/2003 | Schlapfer et al. |
| 6,595,992 | B1 | 7/2003 | Wagner et al. |
| 6,613,050 | B1 | 9/2003 | Wagner et al. |
| 6,623,485 | B2 | 9/2003 | Doubler et al. |
| 6,626,906 | B1 | 9/2003 | Young |
| 6,626,908 | B2 | 9/2003 | Cooper et al. |
| 6,641,586 | B2 | 11/2003 | Varieur |
| 6,652,526 | B1 | 11/2003 | Arafiles |
| 6,660,004 | B2 | 12/2003 | Barker et al. |
| 6,660,006 | B2 | 12/2003 | Markworth et al. |
| 6,695,843 | B2 | 2/2004 | Biedermann et al. |
| 6,702,817 | B2 | 3/2004 | Beger et al. |
| 6,706,045 | B2 | 3/2004 | Lin et al. |
| 6,716,214 | B1 | 4/2004 | Jackson |
| 6,723,100 | B2 | 4/2004 | Biedermann et al. |
| 6,730,092 | B2 | 5/2004 | Songer |
| 6,736,820 | B2 | 5/2004 | Biedermann et al. |
| 6,740,086 | B2 | 5/2004 | Richelsoph |
| 6,755,829 | B1 | 6/2004 | Bono et al. |
| 6,755,835 | B2 | 6/2004 | Schultheiss et al. |
| 6,783,527 | B2 | 8/2004 | Drewry et al. |
| 6,786,907 | B2 | 9/2004 | Lange |
| 6,835,196 | B2 | 12/2004 | Biedermann et al. |
| 6,843,791 | B2 | 1/2005 | Serhan |
| 6,858,030 | B2 | 2/2005 | Martin et al. |
| 6,858,031 | B2 | 2/2005 | Morrison et al. |
| 6,869,432 | B2 | 3/2005 | Schlapfer et al. |
| 6,869,433 | B2 | 3/2005 | Glascott |
| 6,887,242 | B2 | 5/2005 | Doubler et al. |
| 6,896,677 | B1 | 5/2005 | Lin |
| 6,905,500 | B2 | 6/2005 | Jeon et al. |
| 6,918,911 | B2 | 7/2005 | Biedermann et al. |
| 6,951,561 | B2 | 10/2005 | Warren et al. |
| 6,964,664 | B2 | 11/2005 | Fried et al. |
| 6,964,666 | B2 | 11/2005 | Jackson |
| 7,018,379 | B2 | 3/2006 | Drewry et al. |
| 7,022,122 | B2 | 4/2006 | Amrein et al. |
| RE39,089 | E | 5/2006 | Ralph et al. |
| 7,141,051 | B2 | 11/2006 | Janowski et al. |
| 7,186,255 | B2 * | 3/2007 | Baynham et al. ............. 606/266 |
| 7,223,268 | B2 | 5/2007 | Biedermann |
| 7,250,052 | B2 | 7/2007 | Landry et al. |
| 7,476,239 | B2 * | 1/2009 | Jackson ....................... 606/266 |
| 7,530,992 | B2 * | 5/2009 | Biedermann et al. ......... 606/272 |
| 7,625,394 | B2 | 12/2009 | Molz, IV et al. |
| 7,691,129 | B2 * | 4/2010 | Felix ............................ 606/246 |
| 7,691,132 | B2 | 4/2010 | Landry et al. |
| 7,744,635 | B2 | 6/2010 | Sweeney et al. |
| 7,776,040 | B2 | 8/2010 | Markworth et al. |
| 2001/0001119 | A1 | 5/2001 | Lombardo |
| 2002/0010467 | A1 | 1/2002 | Cooper et al. |
| 2002/0022842 | A1 | 2/2002 | Horvath et al. |
| 2002/0026193 | A1 | 2/2002 | Barker et al. |
| 2002/0035366 | A1 | 3/2002 | Walder et al. |
| 2002/0058942 | A1 | 5/2002 | Biedermann et al. |
| 2002/0082602 | A1 | 6/2002 | Biedermann et al. |
| 2002/0091386 | A1 | 7/2002 | Martin et al. |
| 2002/0120272 | A1 | 8/2002 | Yuan |
| 2002/0133154 | A1 | 9/2002 | Saint Martin |

| | | |
|---|---|---|
| 2002/0138076 A1 | 9/2002 | Biedermann et al. |
| 2002/0143341 A1 | 10/2002 | Biedermann et al. |
| 2002/0151900 A1 | 10/2002 | Glascott |
| 2002/0183748 A1 | 12/2002 | Martin et al. |
| 2003/0004512 A1 | 1/2003 | Farris et al. |
| 2003/0023243 A1 | 1/2003 | Biedermann et al. |
| 2003/0032957 A1 | 2/2003 | McKinley |
| 2003/0073996 A1 | 4/2003 | Doubler et al. |
| 2003/0073997 A1 | 4/2003 | Doubler et al. |
| 2003/0083657 A1 | 5/2003 | Drewry et al. |
| 2003/0100896 A1 | 5/2003 | Biedermann et al. |
| 2003/0100904 A1 | 5/2003 | Biedermann |
| 2003/0125741 A1 | 7/2003 | Biedermann et al. |
| 2003/0149431 A1 | 8/2003 | Varieur |
| 2003/0158552 A1 | 8/2003 | Jeon et al. |
| 2003/0187439 A1 | 10/2003 | Biedermann et al. |
| 2003/0187442 A1 | 10/2003 | Richelsoph et al. |
| 2003/0199873 A1 | 10/2003 | Richelsoph |
| 2004/0030337 A1 | 2/2004 | Alleyne et al. |
| 2004/0097933 A1 | 5/2004 | Lourdel et al. |
| 2004/0102781 A1 | 5/2004 | Jeon |
| 2004/0116929 A1 | 6/2004 | Barker |
| 2004/0138660 A1 | 7/2004 | Serhan |
| 2004/0138662 A1 | 7/2004 | Landry et al. |
| 2004/0143265 A1 | 7/2004 | Landry et al. |
| 2004/0153077 A1 | 8/2004 | Biedermann et al. |
| 2004/0158247 A1 | 8/2004 | Sitiso et al. |
| 2004/0172022 A1 | 9/2004 | Landry et al. |
| 2004/0172025 A1 | 9/2004 | Drewry et al. |
| 2004/0181224 A1 | 9/2004 | Biedermann et al. |
| 2004/0186473 A1 | 9/2004 | Cournoyer et al. |
| 2004/0186474 A1 | 9/2004 | Matthis et al. |
| 2004/0193160 A1 | 9/2004 | Richelsoph |
| 2004/0225289 A1 | 11/2004 | Biedermann et al. |
| 2004/0230192 A1 | 11/2004 | Graf |
| 2004/0236330 A1 | 11/2004 | Purcell et al. |
| 2004/0249378 A1 | 12/2004 | Saint Martin et al. |
| 2004/0249380 A1 | 12/2004 | Glascott |
| 2004/0260283 A1 | 12/2004 | Wu et al. |
| 2004/0260284 A1 | 12/2004 | Parker |
| 2004/0267264 A1 | 12/2004 | Konieczynski et al. |
| 2005/0010218 A1 | 1/2005 | Dalton |
| 2005/0010219 A1 | 1/2005 | Dalton |
| 2005/0033296 A1 | 2/2005 | Bono et al. |
| 2005/0033298 A1 | 2/2005 | Hawkes et al. |
| 2005/0038430 A1 | 2/2005 | McKinley |
| 2005/0049588 A1 | 3/2005 | Jackson |
| 2005/0049589 A1 | 3/2005 | Jackson |
| 2005/0055026 A1 | 3/2005 | Biedermann et al. |
| 2005/0070899 A1 | 3/2005 | Doubler et al. |
| 2005/0070901 A1 | 3/2005 | David |
| 2005/0080415 A1 | 4/2005 | Keyer et al. |
| 2005/0080420 A1 | 4/2005 | Farris et al. |
| 2005/0085812 A1 | 4/2005 | Sherman et al. |
| 2005/0119658 A1 | 6/2005 | Ralph et al. |
| 2005/0131410 A1 | 6/2005 | Lin |
| 2005/0137594 A1 | 6/2005 | Doubler et al. |
| 2005/0154389 A1 | 7/2005 | Selover et al. |
| 2005/0154391 A1 | 7/2005 | Doherty et al. |
| 2005/0171542 A1 | 8/2005 | Biedermann et al. |
| 2005/0177154 A1 | 8/2005 | Moumene et al. |
| 2005/0187548 A1 | 8/2005 | Butler et al. |
| 2005/0187555 A1 | 8/2005 | Biedermann |
| 2005/0192571 A1 | 9/2005 | Abdelgany |
| 2005/0192573 A1 | 9/2005 | Abdelgany et al. |
| 2005/0192580 A1 | 9/2005 | Dalton |
| 2005/0192589 A1 | 9/2005 | Raymond et al. |
| 2005/0203515 A1 | 9/2005 | Doherty et al. |
| 2005/0203516 A1 | 9/2005 | Biedermann et al. |
| 2005/0216003 A1 | 9/2005 | Biedermann et al. |
| 2005/0228379 A1 | 10/2005 | Jackson |
| 2005/0228382 A1 | 10/2005 | Richelsoph |
| 2005/0240180 A1 | 10/2005 | Vienney et al. |
| 2005/0251139 A1 | 11/2005 | Roh |
| 2005/0261687 A1 | 11/2005 | Garamszegi et al. |
| 2005/0267472 A1 | 12/2005 | Biedermann et al. |
| 2005/0277923 A1 | 12/2005 | Sweeney |
| 2005/0277928 A1 | 12/2005 | Boschert |
| 2005/0277931 A1 | 12/2005 | Sweeney et al. |
| 2005/0283157 A1 | 12/2005 | Coates et al. |
| 2005/0288671 A1 | 12/2005 | Yuan |
| 2006/0036242 A1 | 2/2006 | Nilsson et al. |
| 2006/0036244 A1 | 2/2006 | Spitler et al. |
| 2006/0036252 A1 | 2/2006 | Baynham et al. |
| 2006/0036260 A1 | 2/2006 | Runco et al. |
| 2006/0052783 A1 | 3/2006 | Dant et al. |
| 2006/0052784 A1 | 3/2006 | Dant et al. |
| 2006/0058788 A1 | 3/2006 | Hammer et al. |
| 2006/0074419 A1 | 4/2006 | Taylor et al. |
| 2006/0084979 A1 | 4/2006 | Jackson |
| 2006/0084980 A1 | 4/2006 | Melkent et al. |
| 2006/0084981 A1 | 4/2006 | Shluzas |
| 2006/0084993 A1 | 4/2006 | Landry et al. |
| 2006/0142761 A1 | 6/2006 | Landry et al. |
| 2006/0149245 A1 | 7/2006 | Sweeney |
| 2006/0200128 A1 | 9/2006 | Mueller |
| 2007/0055235 A1 | 3/2007 | Janowski et al. |

FOREIGN PATENT DOCUMENTS

| | | |
|---|---|---|
| WO | WO-0152758 | 7/2001 |

OTHER PUBLICATIONS

PCT/US2004/010319 Written Opinion of the International Searching Authority—Oct. 14, 2004.

PCT/US2004/010319 International Preliminary Report on Patentability—Oct. 14, 2005.

* cited by examiner

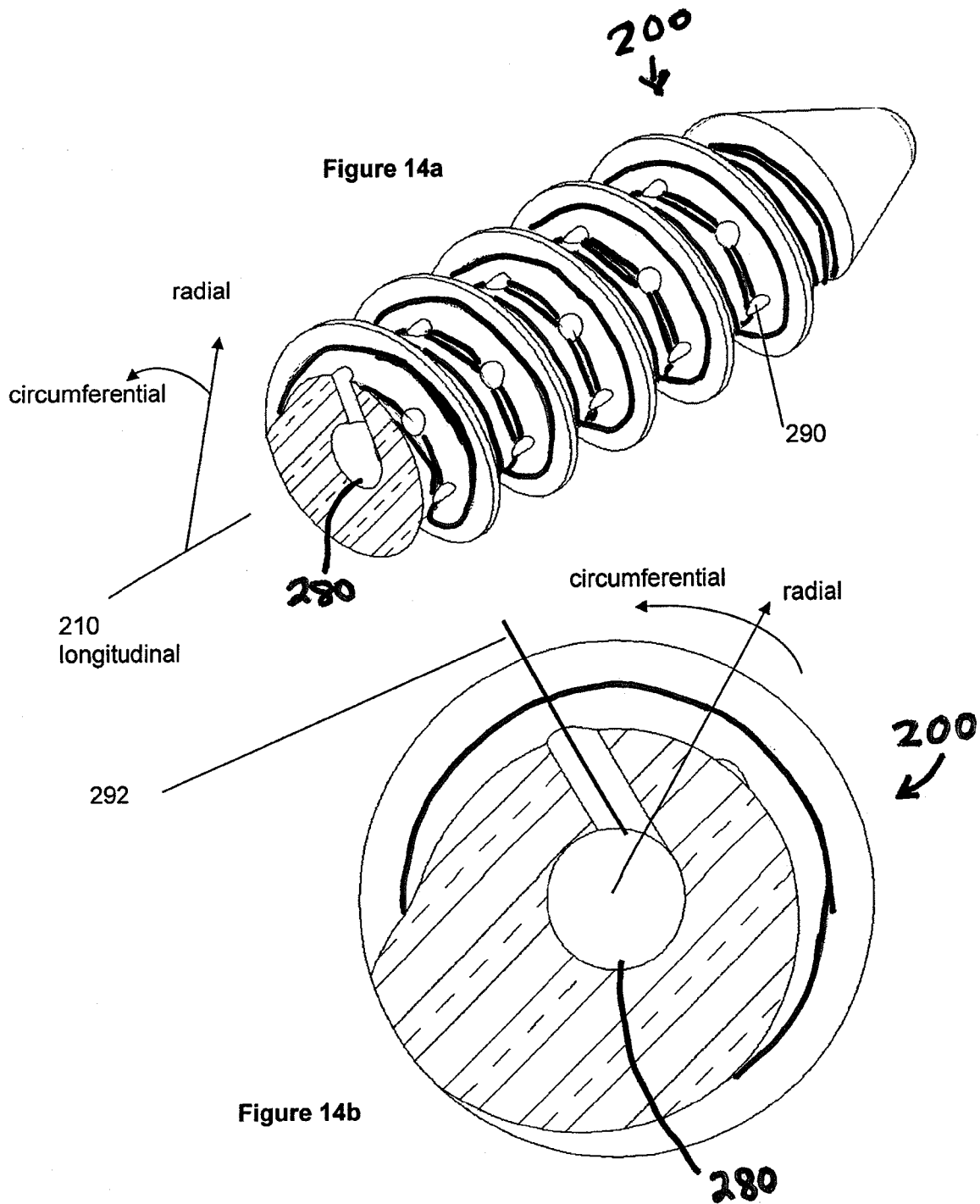

FRICTIONAL POLYAXIAL SCREW ASSEMBLY

REFERENCE TO RELATED APPLICATIONS

This application claims priority to and benefit under 35 U.S.C. §119(e) to U.S. Provisional App. No. 60/916,659, entitled "Frictional Polyaxial Screw Assembly," filed May 8, 2007, the entire contents of which is herein incorporated by reference. This application also claims priority to and benefit under 35 U.S.C. §119(e) to U.S. Provisional App. No. 60/939,977, entitled "Frictional Polyaxial Fenestrated Screw Assembly," filed May 24, 2007, the entire contents of which is herein incorporated by reference.

TECHNICAL FIELD

Disclosed embodiments pertain to spinal surgery.

BACKGROUND

In spinal hardware, there are various features that have been incorporated into screws. Simple forms of polyaxial screws have had a head and a shaft that may easily and loosely pivot relative to each other within a defined range of angles.

BRIEF DESCRIPTION

Embodiments are provided that include a polyaxial spinal screw assembly that has a threaded screw with a bulbous or curvate head, and a receiver, and a slotted collet between the receiver and the screw head. The curvate head may be a portion of a sphere. The collet may, in an un-locked condition, bear against the head of the screw to frictionally retain the screw's angular position. The points of contact with the collet, in an un-locked condition, may include a contact point of the screw head against the collet interior that may be at or near a maximum diameter of the screw head. Additionally, there may be two other contact points of the outside of the collet against the interior of the receiver. These contact points may be respectively located in opposite directions along the axial direction of the collet from the earlier-described contact point. This may create a three-point bending condition in the wall of the collet, when the assembly is in an assembled but untightened condition. The collet may be able to elastically bend to accommodate assembly and to apply force to the screw head, in an un-locked condition, for the purpose of creating friction to retain a desired relative position of the screw and the receiver.

The screw head may be able to be inserted into the receiver through the bottom of the receiver, i.e., in the absence of the collet, the screw head and entire body of the screw may be able to pass through the receiver.

Other embodiments may include a collet that may be slotted, such as having slots that come into the collet in a generally axial direction alternately from opposite directions creating a zig-zag pattern of material remaining in the collet. Some of the slots may create interruptions in the axially-facing surface of the collet against which a spinal rod bears when the assembly is tightened. The collet may have a lip, such as a radially-outward-pointing lip, capable of interacting with a corresponding feature of the receiver such as a recess of the receiver. This interaction may contribute to a capturing of the collet in the receiver. The collet may have an external surface that is curved in two directions. Tightening of the assembly may result from a spinal rod pushing against the top of the collet urging it farther into a cavity in the receiver.

The screw in the described polyaxial screw assembly may be cannulated and also may be fenestrated. A non-fenestrated screw may have a longitudinal hole that extends the entire length of the screw (a through-hole). A fenestrated screw may have a blind longitudinal hole that intersects the fenestration holes. Fenestration holes may be clustered toward the distal end of the screw and may kept to a somewhat small fenestration hole diameter so as to limit the dimension of possible pillars of hardened resin originating from the holes. Embodiments may also be provided with a bone screw of any design that may have fenestration holes that include a component in the rotational direction of the screw, such as holes that are somewhat backward-facing with respect to the forward-rotational direction of the screw. This feature may be used in any type of bone screw.

BRIEF DESCRIPTION OF THE ILLUSTRATIONS

Embodiments are illustrated in the following Figures.

FIG. 1a is a three-dimensional view of a screw of a particular embodiment. FIG. 1b is a three-dimensional view of the screw of FIG. 1a cut in half. In FIG. 1b, the screw is solid.

Figure 6B:
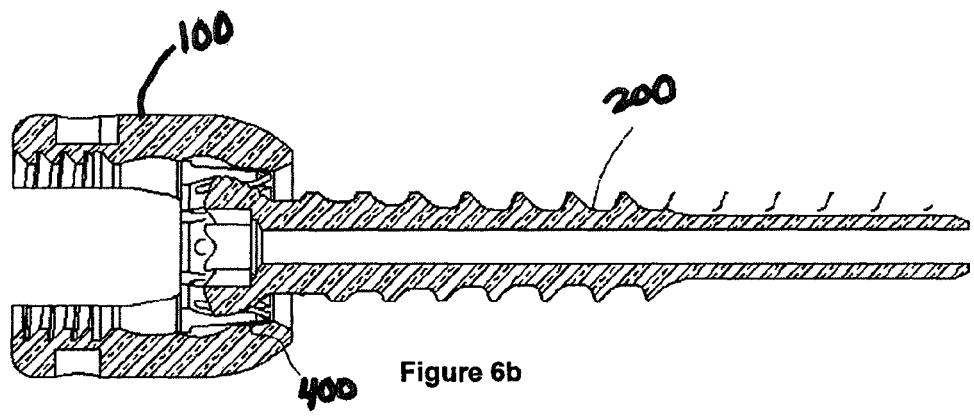
Figure 6A:
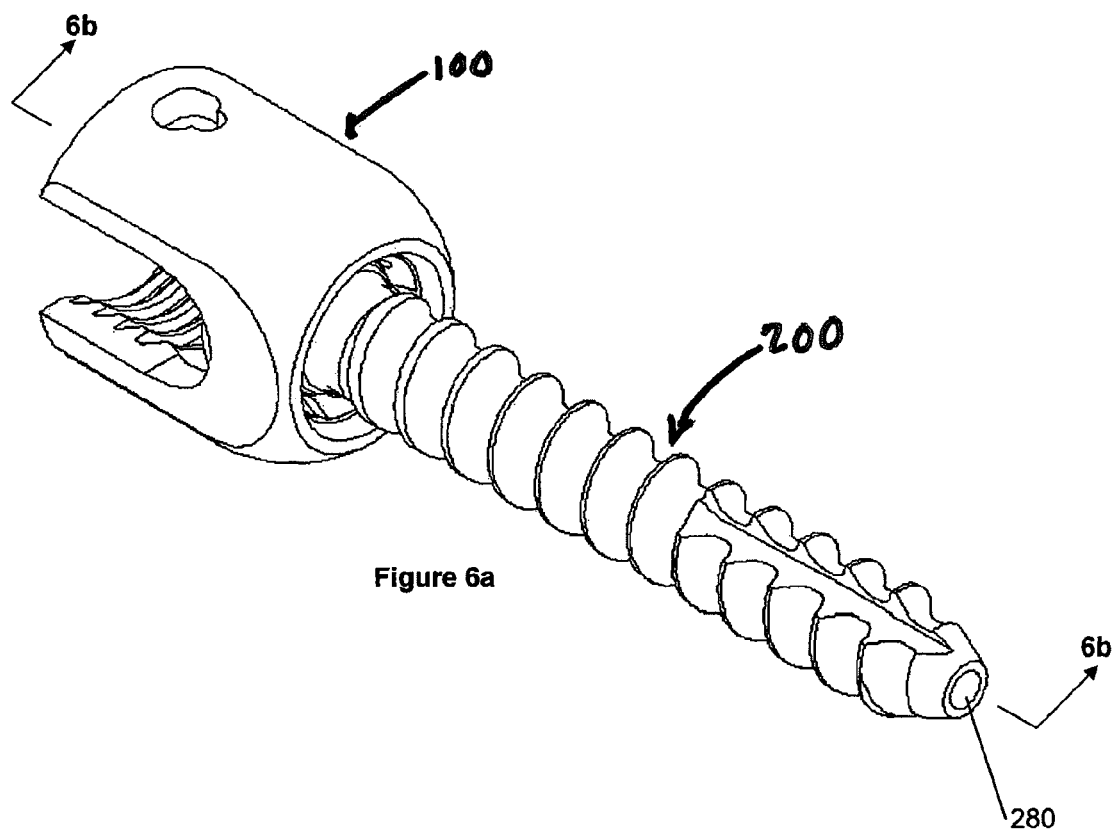

FIG. 6a is a three-dimensional view of a screw assembly of a particular embodiment. FIG. 6b is a cross-section of FIG. 6a. The screw in FIGS. 6a and 6b is cannulated.

Figure 7:
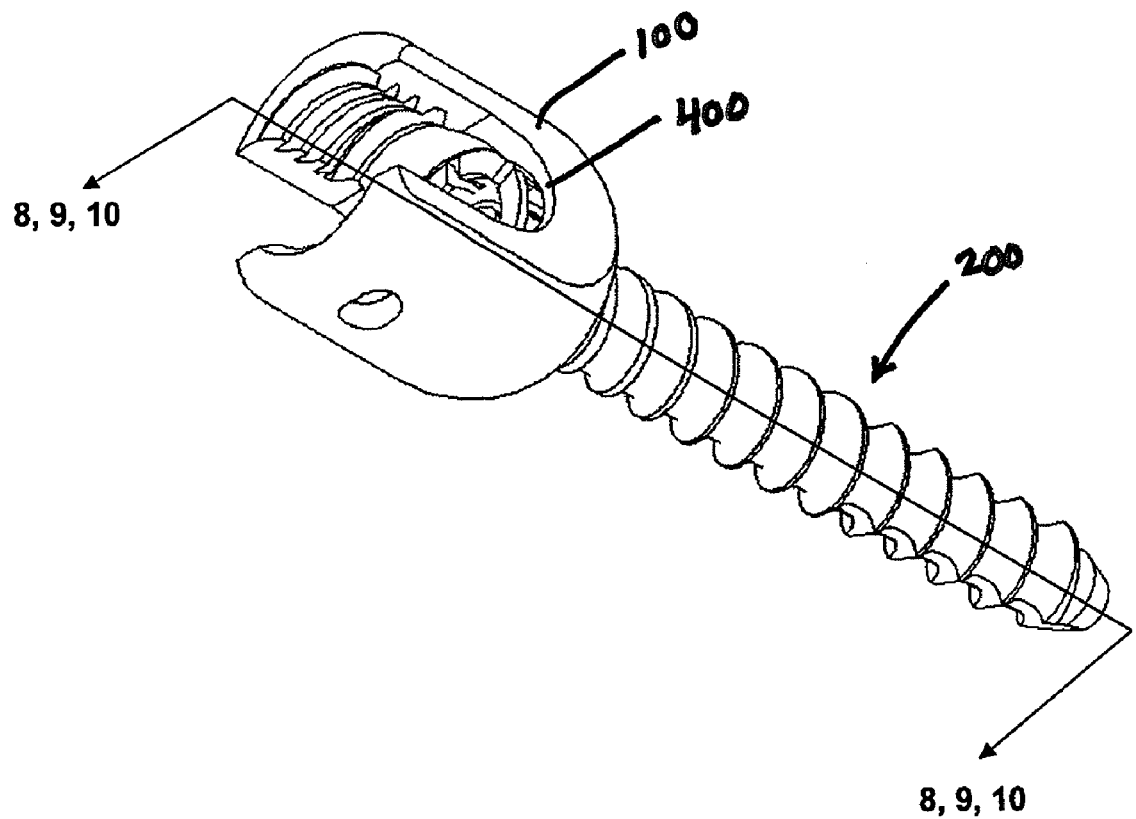

FIG. 7 is a three-dimensional view of a screw assembly of a particular embodiment.

Figure 8:
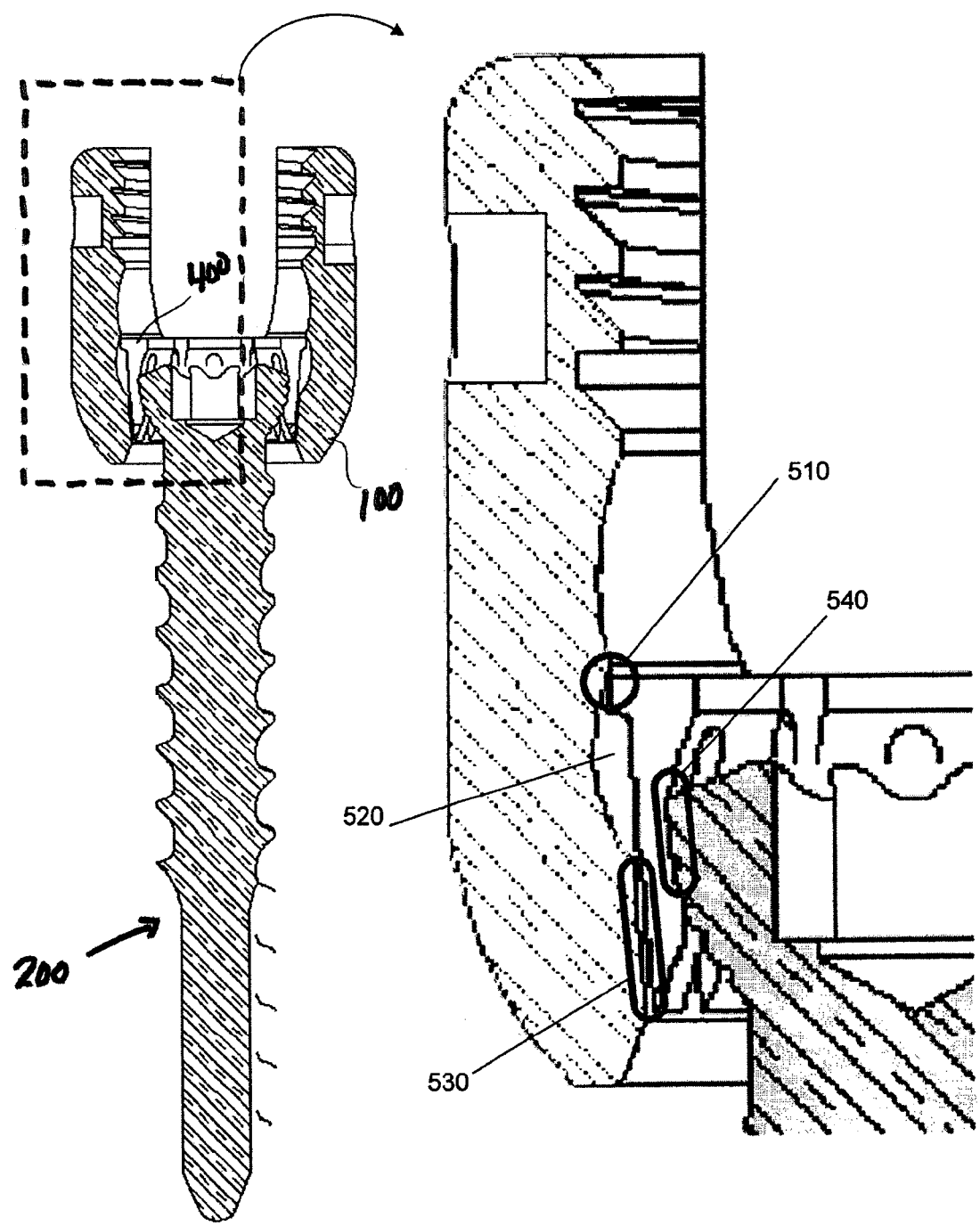

FIG. 8 is a cross-section of the assembly FIG. 7, the screw in this Figure being solid. FIG. 8 illustrates the condition where the relative positions of the screw and the receiver may be adjusted. Also shown is an enlargement of a region of that cross-section.

Figure 9:
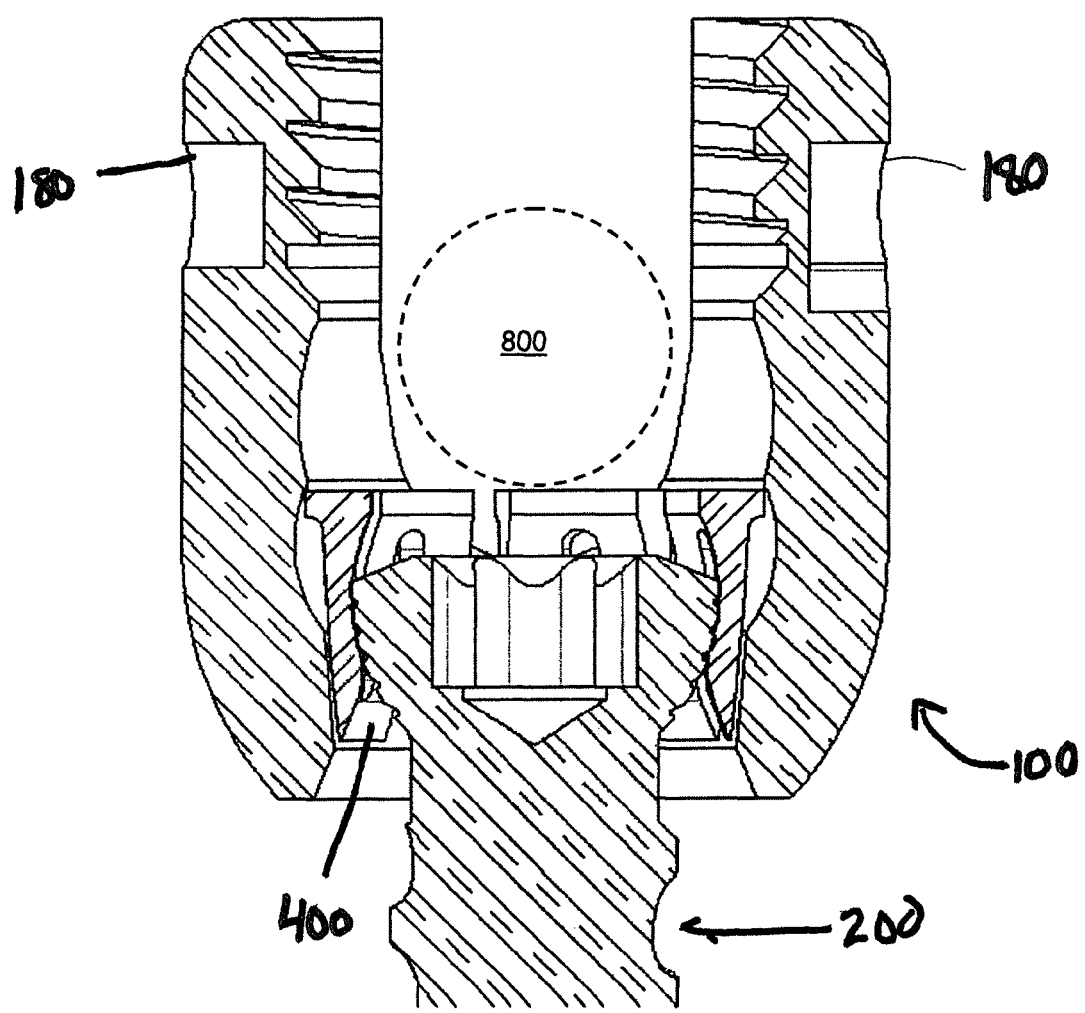

FIG. 9 is similar to FIG. 8 also showing an enlargement of a region of the cross-section of FIG. 8.

Figure 10:
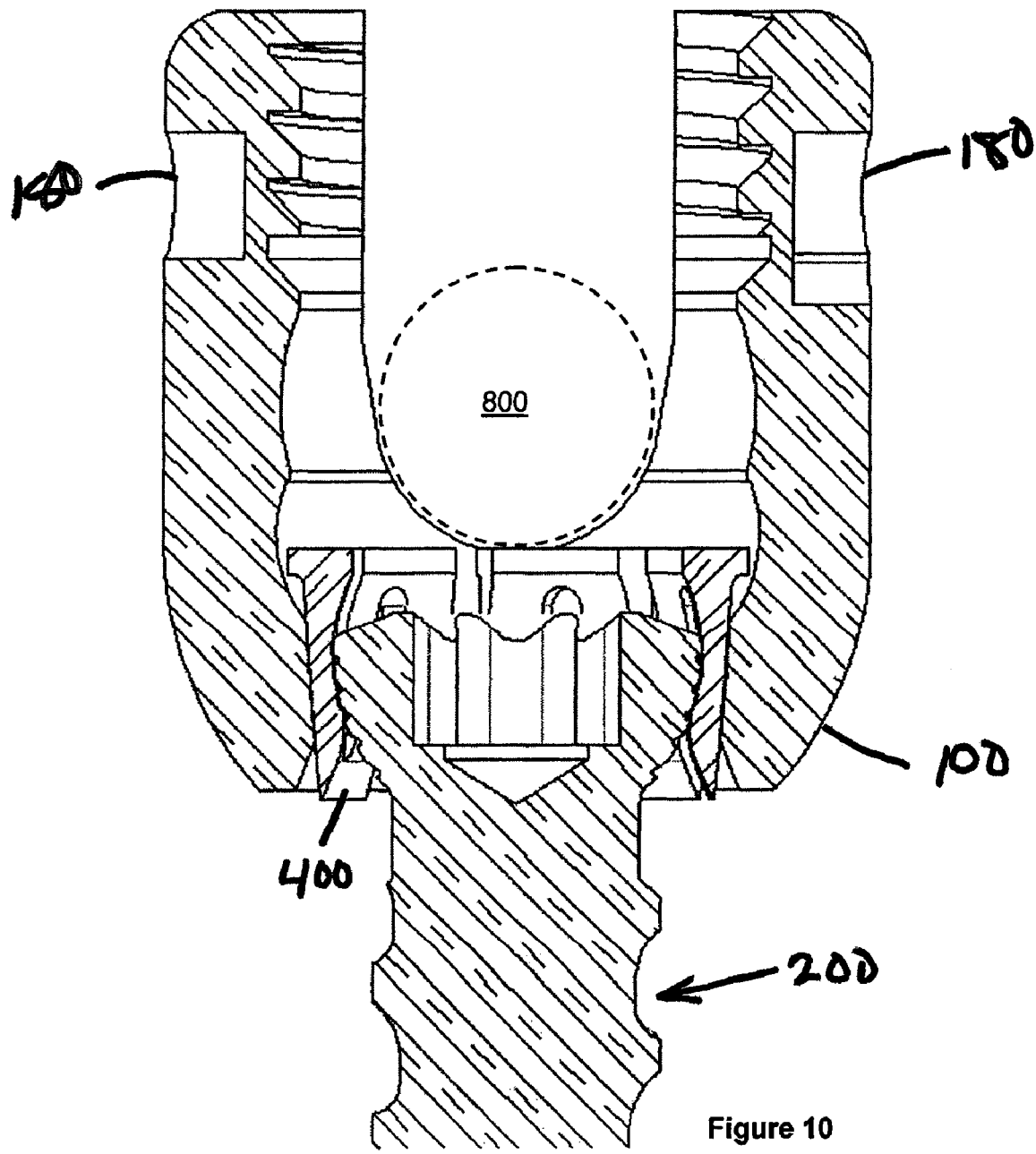

FIG. 10 shows the assembly of FIG. 8 in the condition wherein the parts have been locked due to downward advancement of the collet.

Figure 11:
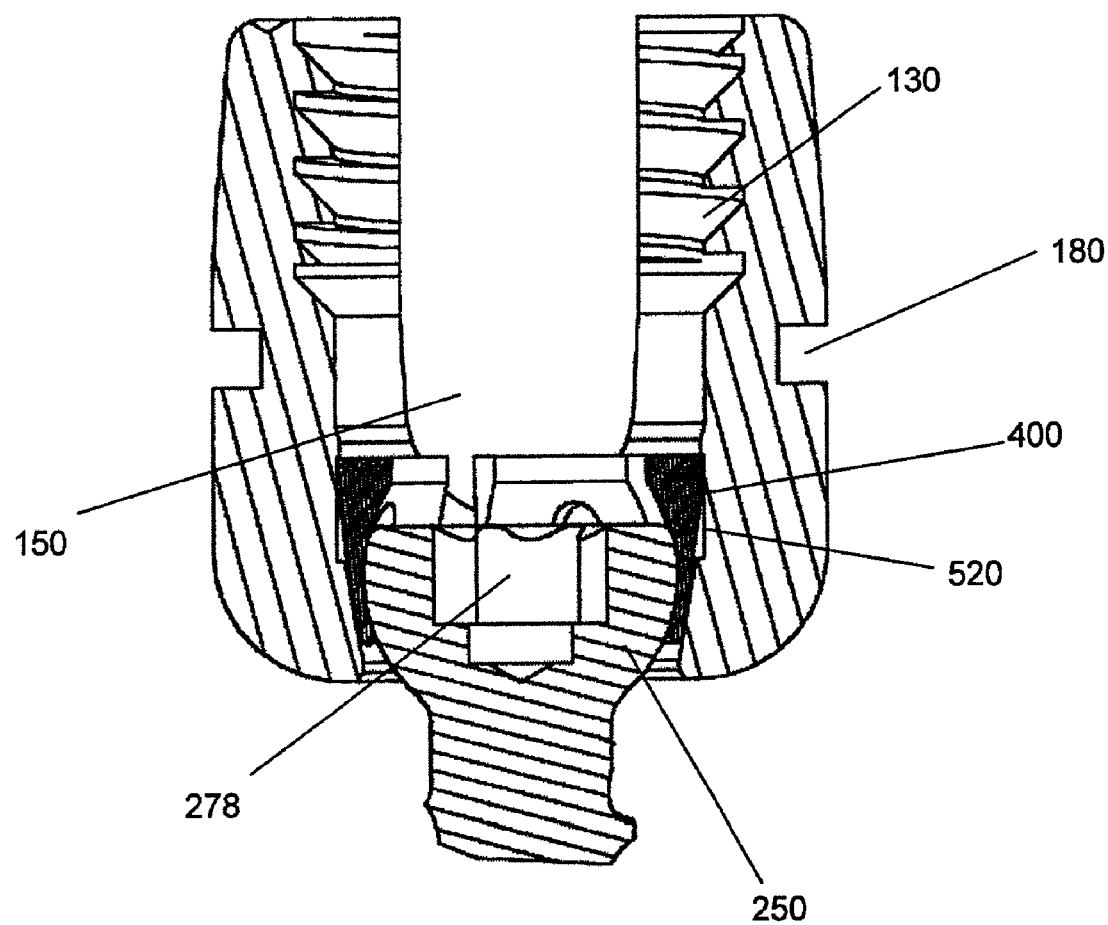

FIG. 11 is a cross-section of yet another design having many of the already-described features but without the ability to be assembled from the bottom.

Figure 12A:
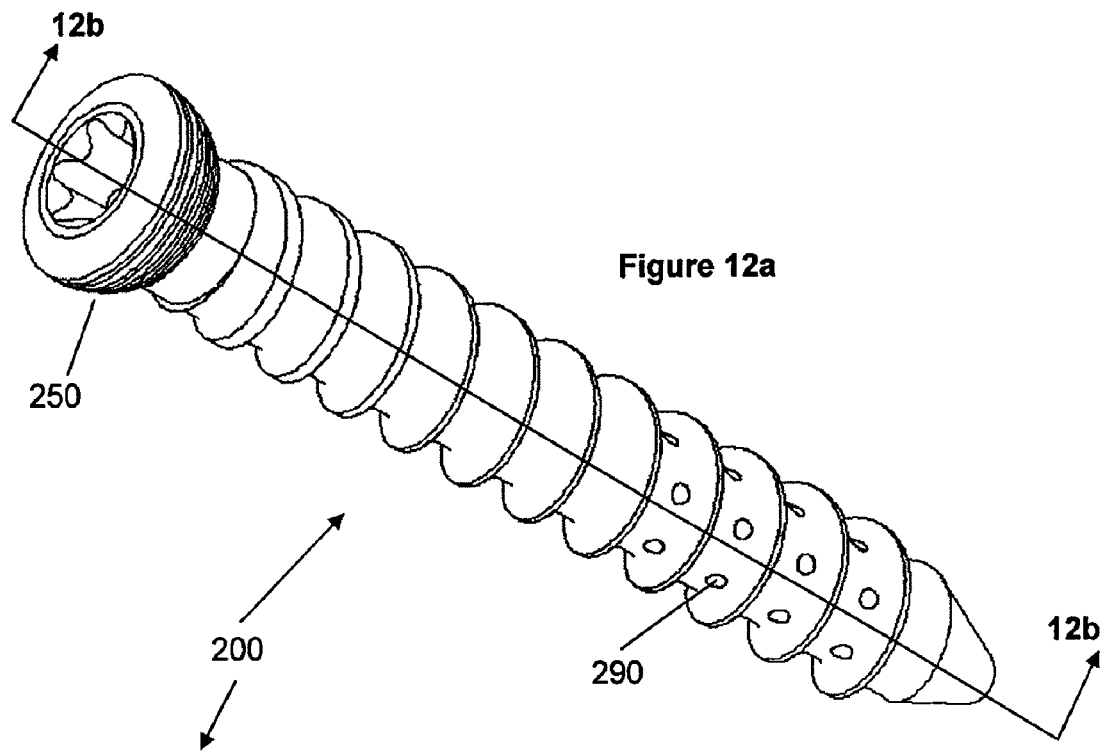
Figure 12B:
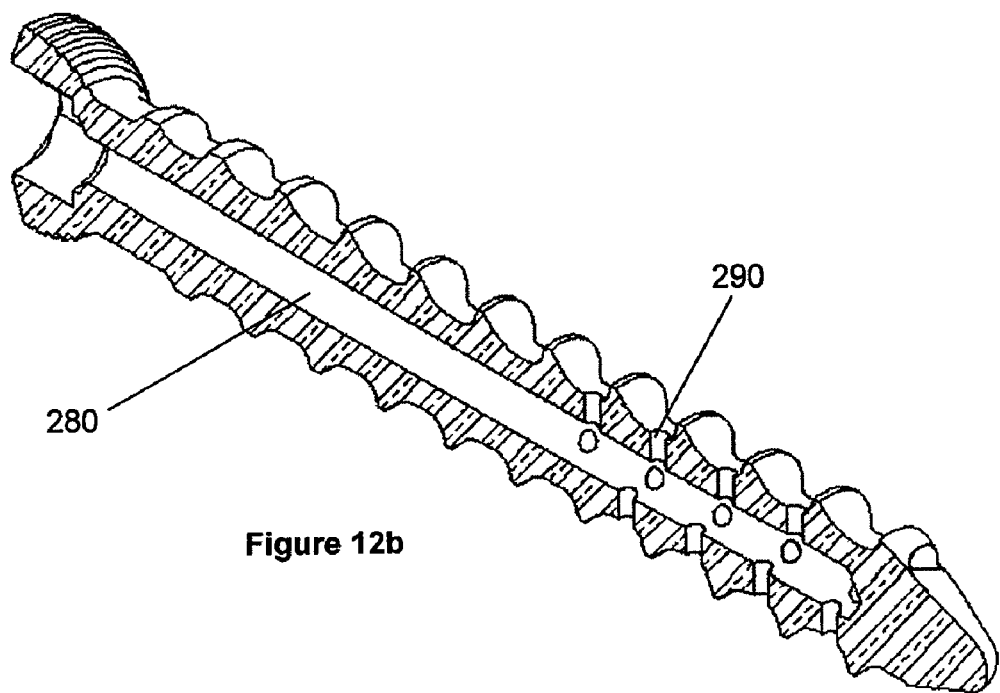

FIG. 12a is a three-dimensional illustration of a screw of a particular embodiment, in which the screw is cannulated with a blind hole and also has fenestrations. FIG. 12b is a three-dimensional view of the screw of FIG. 12a, cut in half.

Figures 13A, 13B:
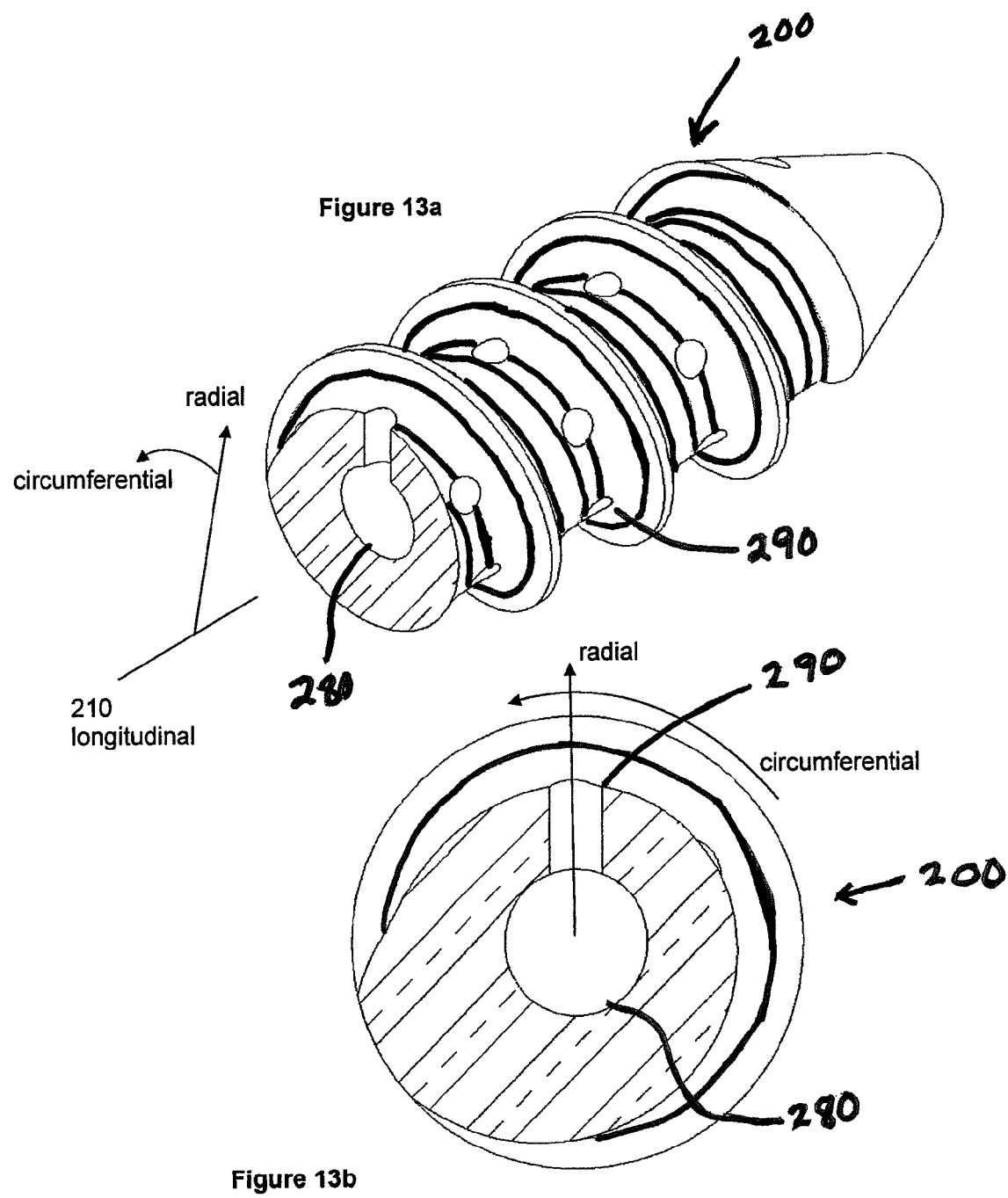

FIG. 13a is a three-dimensional view of the screw of FIG. 12, cut perpendicular to its lengthwise axis. FIG. 13b is a straight-on view of FIG. 13a. In FIG. 13, the fenestration holes are radially oriented.

FIG. 14a is a three-dimensional view of a screw of a particular embodiment, cut perpendicular to its lengthwise axis. FIG. 14b is a straight-on view of FIG. 14a. In FIG. 14, the fenestration holes have a circumferential component to them, in addition to a radial component.

Figure 15:
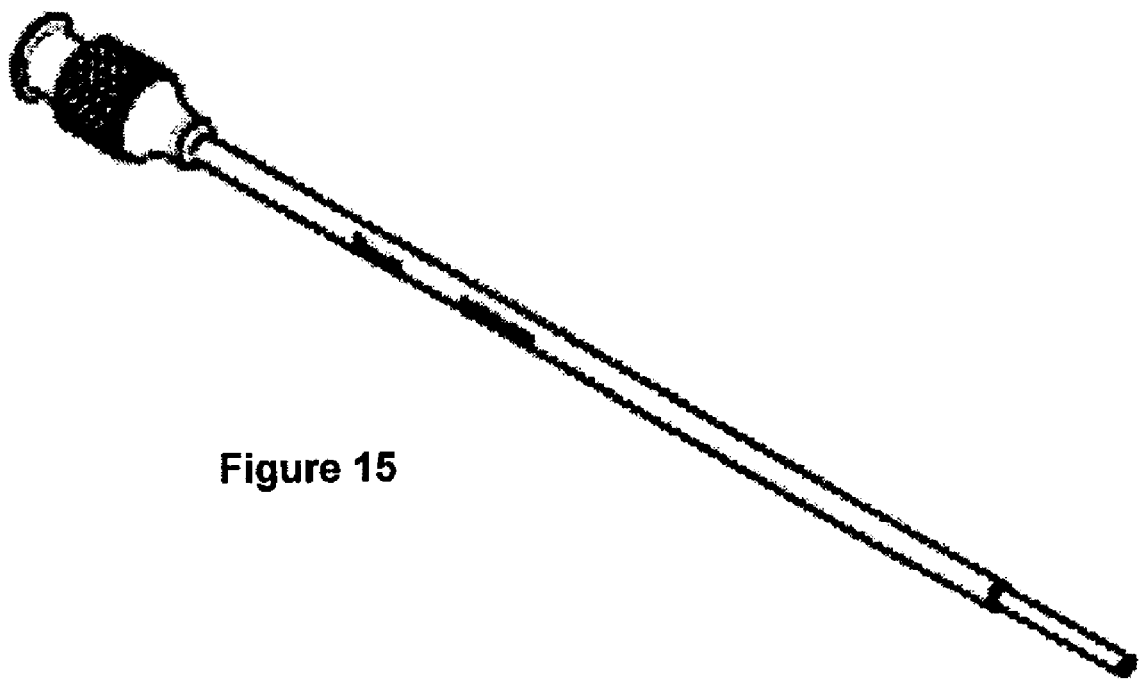

FIG. 15 is an illustration of an injector tube for use in injecting a fluid such as resin or dye into the central hole of a cannulated or cannulated and fenestrated screw.

DETAILED DESCRIPTION

Various embodiments may be provided with a polyaxial screw assembly comprising a screw 200, and a collet 400, and a receiver 100 having a cavity 150.

Screw

Figure 1A:
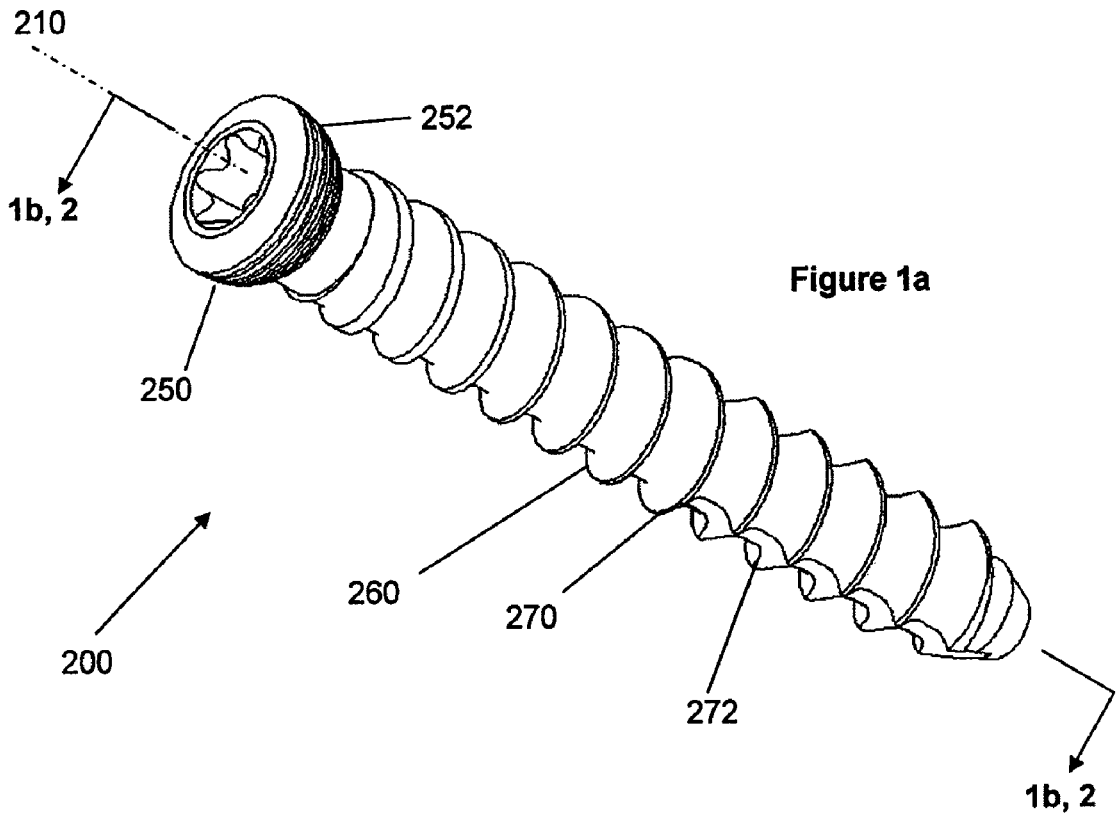
Figure 1B:
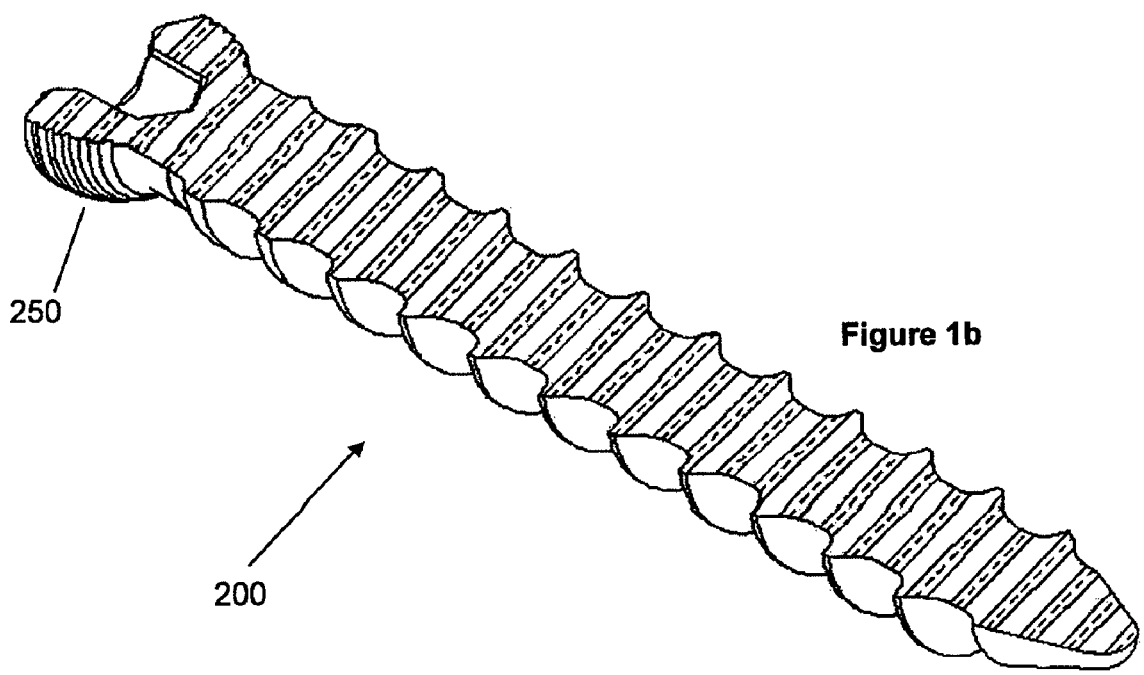
Figure 2:
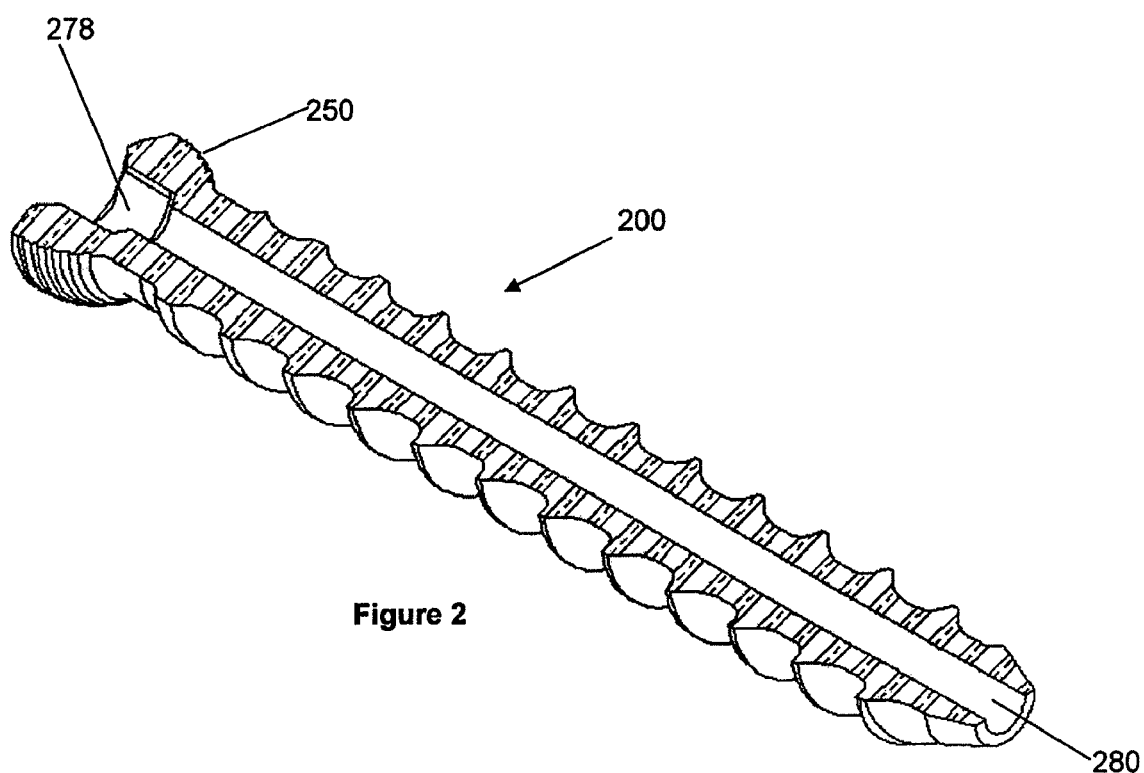
FIG. 2 is a three-dimensional view of a cannulated screw that has been cut in half.

Referring now to FIGS. 1 and 2, the screw 200 may comprise a head 250 and a shaft 260 extending from the head 250. The screw head 250 may have a maximum diameter that is larger than any diameter of the shaft 260. The screw head 250 may have a generally curved surface at least on the side that faces the shaft 260. This surface may include grooves 252 at a smaller size scale than the screw head itself for enhancing gripping of the screw head in a final locked condition. The envelope of screw head 250 (enveloping any possible grooves 252) may be a portion of a sphere, although the sphere may be truncated. Screw head 250 may be generally axisymmetric around a screw axis 210 except for possible localized features such as a tooling recess. Screw head 250 may comprise a tooling recess 278 such as a hex or a Torx® shape suitable to interact with an installation tool.

The shaft 260 may be at least partially threaded having threads 270 that may be helical threads. Threads 270 near the tip of shaft 260 may be interrupted so as to form a self-tapping cutting surface 272. Shaft 260 may be generally axisymmetric around screw axis 210 with the exception of localized features such as thread details and tooling recess 278.

One possibility is that screw 200 may be solid as illustrated in FIG. 1. Another possibility, illustrated in FIG. 2, is that screw 200 may be cannulated through the length of shaft 260 and head 250, having a longitudinal hole 280 that may coincide with axis 210. The longitudinal hole 280 may be of a diameter appropriate to accept a guide wire such as a K-wire (Kirschner wire). Alternatively or in addition, longitudinal hole 280 may be suitable for injecting or delivering a flowable liquid to the bone in the vicinity of the screw shaft 260. Longitudinal hole 280 may intersect with and may be substantially coaxial with tooling recess 278 (if present). There may be a suitable geometric transition between longitudinal hole 280 and tooling recess 278.

Collet

Figure 3A:
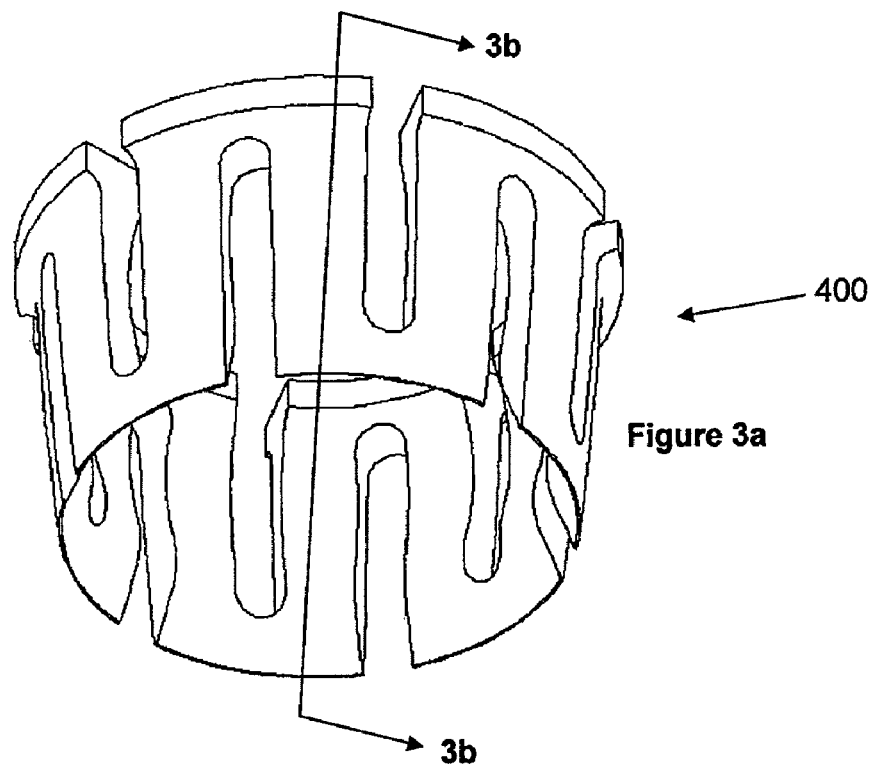
FIG. 3a is a three-dimensional view of a collet used in various embodiments.
Figure 3B:
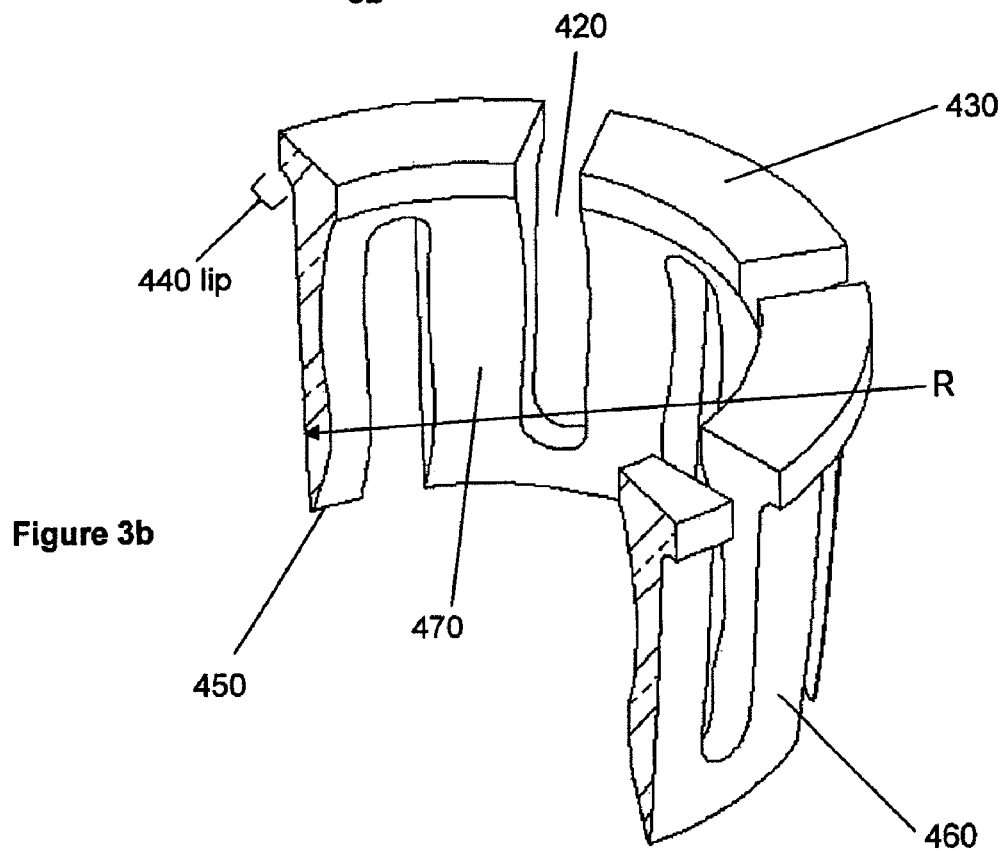
FIG. 3b is a three-dimensional view of the collet of FIG. 3a, cut in half for purposes of illustration.

Referring now to FIG. 3, collet 400 may have an external surface or external surface envelope 460, and may have an internal surface or internal surface envelope 470. These surfaces or envelopes may be substantially axisymmetric except for the absence of material due to slots 420. Either or both of external surface 460 and internal surface 470 may be curved in more than one direction; or, alternatively, one or both might be frustoconical. Internal surface 470, or the envelope thereof, may be a portion of a sphere. These surfaces may together define a collet wall (whose thickness may be non-uniform). In this collet wall there may be a plurality of axially-oriented slots 420. Some of the slots 420 may advance from a first end 430 of collet 400 and others of slots 420 may advance from a second end 450 of collet 400. Slots 420 may advance in alternating directions from respective ends of collet 400. (As another possibility, arrays of slots 420 from a single direction are also possible.) These slots 420 may give collet 400 the ability to be stretched or otherwise deformed to dimensions larger than its natural dimensions, or to be squeezed to dimensions smaller than its natural dimensions, and then to spring back when released. The collet 400 may be capable of elastic deformation to permit the snapping and retention and to provide frictional force bearing against screw head 250. The collet 400 may further have an end surface 430 that may be interrupted by slots 420. End surface 430, or the envelope of the end surface 430 of collet 400, may comprise a flat surface suitable to be pushed against by a spinal rod 800.

Collet 400 may have a lip 440 oriented at least partially radially outward at the end of collet 400 at which the end surface 430 is located. Lip 440 may be such as to interact with a corresponding internal surface or feature of the cavity 150 (see FIG. 4) of receiver 100 to cause bending or deformation of collet 400. For example, as collet 400 advances into cavity 150, lip 440 may follow the internal surface of cavity 150 to first compress, then expand. The presence of lip 440 extending out to a larger radial position than the rest of collet 440 provides some opportunity for the upper portion of collet 400 near end surface 430 to undergo bending etc. to follow the shape of the cavity internal wall independently of what deformation may or may not occur near the opposite end of collet 400. For example, a radially outward projecting lip 440 makes it possible to impose one radial deformation as a function of axial position on the lower part of the collet 400 and a second, different radial deformation as a function of axial position on the upper part of the collet 400. This may enable control of the amount of bending experienced by the wall of collet 400 in the un-locked condition that relates to the frictional force exerted by the collet 400 on the screw head 250. The lower part of collet 400, being more radially compact than the region containing lip 440, would not have to interact with the wall pattern that the upper part of collet 400 interacts with, because the lower part would be able to simply pass by without interacting. Lip 440 may also help in capturing collet 400 within cavity 150 of receiver 100. However, it is also possible that collet 400 not contain a lip 440.

Receiver

Figures 4A, 4B:
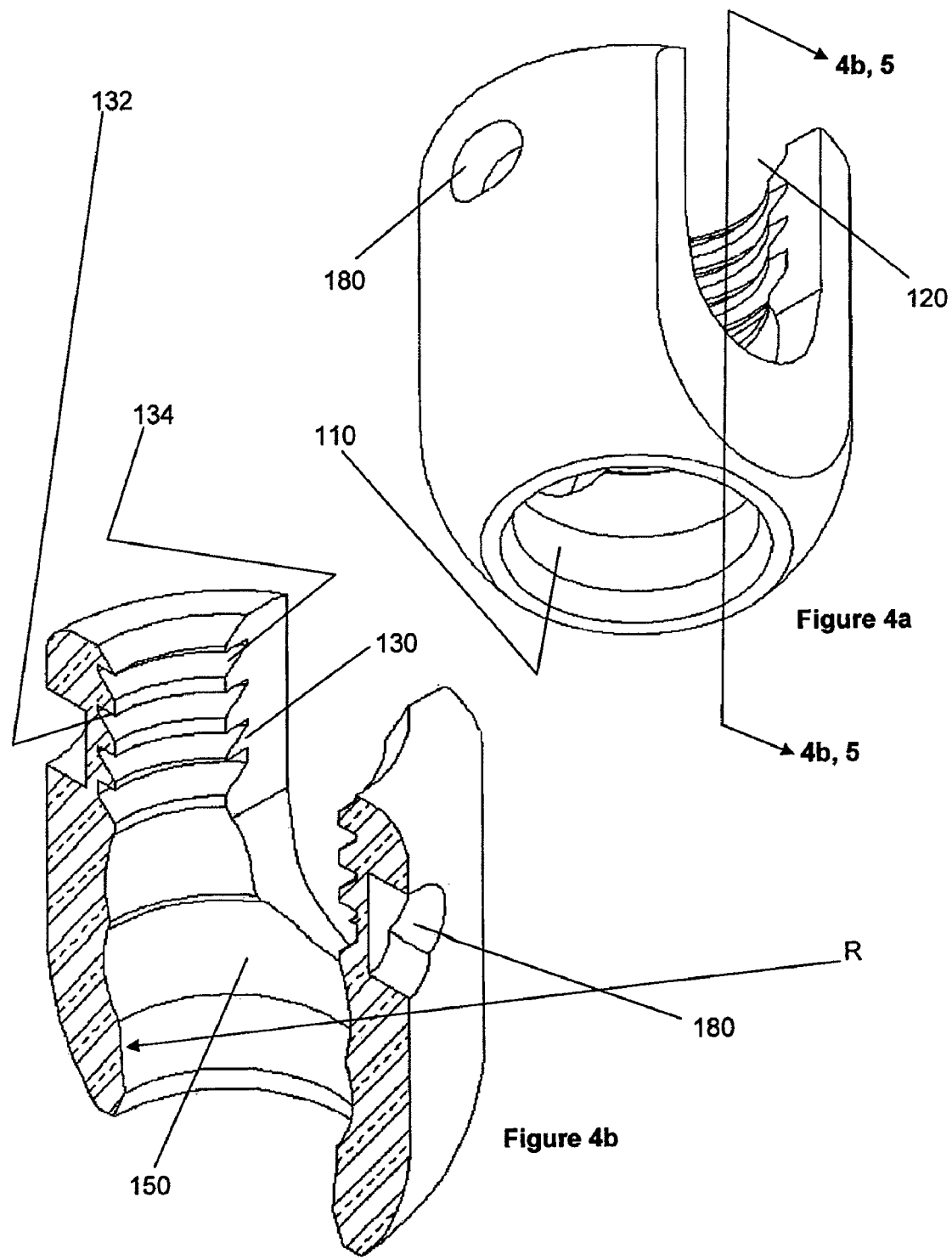
FIG. 4a is a three-dimensional view of a receiver of a particular embodiment.
FIG. 4b is a three-dimensional view of the receiver of FIG. 4a, cut in half for purposes of illustration.
Figure 5:
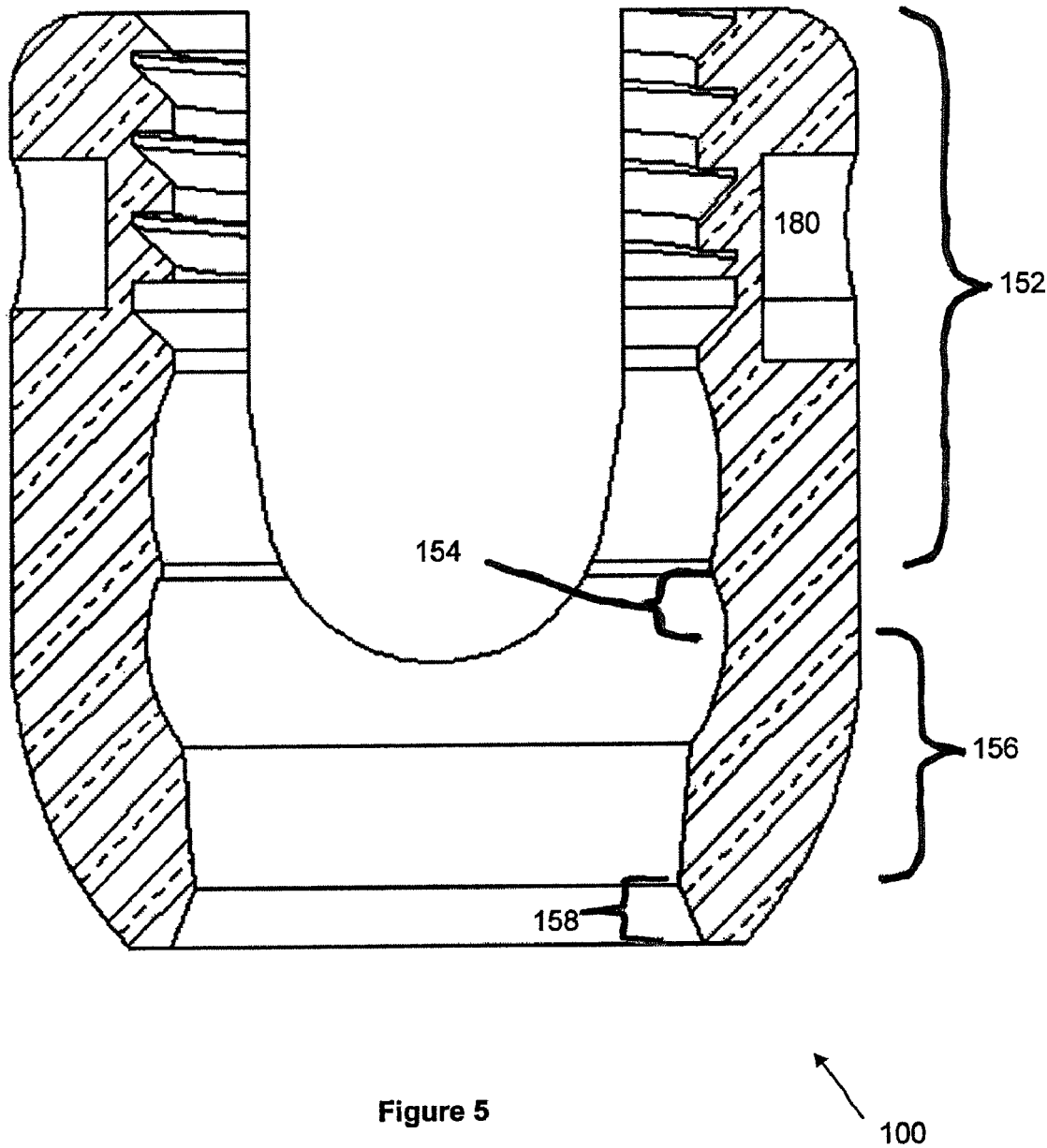
FIG. 5 is a cross-section of the receiver of a particular embodiment.

Referring now to FIGS. 4 and 5, the receiver 100 may have a receiver central hole 110 for accepting screw 200. The receiver 100 may further comprise a U-shaped channel 120, having a lengthwise direction at least approximately transverse to receiver central hole 110, for accepting a spinal rod. Receiver 100 may comprise a thread 130 in receiver central hole 110 for accepting a setscrew to urge the spinal rod 800 into the receiver 100. Thread 130 may, as illustrated, be a buttress thread whose load-bearing surface 132 (in the locked condition) is flat (perpendicular to the axis of the thread 130) and whose non-load-bearing surface 134 is angled. The setscrew (not shown) may comprise a corresponding buttress thread to engage thread 130. The receiver 100 may further have external indentations 180 for cooperating with gripping features of an installation tool or a tool to help urge the spinal rod 800 and receiver 100 into contact with each other.

The receiver 100 may have a cavity 150 suitable to accept collet 400 therein. The cavity 150 may be such that as one progresses into the cavity 150 from the proximal end of receiver 100, there is first of all an entry region 152. Following entry region 152, there may be a diverging region 154. Following diverging region 154 there may be a converging region 156. Following converging region 156 there may be an exit region 158 that may be diverging. Entry region 152 may be considered to include the threaded region containing threads 130, and any other shapes that may be present, prior to the start of diverging region 154. The characteristics of exit region 158 may be chosen so as to determine, at least in part, the allowable range of angulation of the polyaxial screw assembly. Characteristics and dimensional relationships are further discussed elsewhere herein. Also, as best seen in FIG. 5, receiver 100 may further be described as having, as one progresses into the cavity 150 from the proximal end of receiver 100, an internally threaded region having a thread 130, followed by a first concave barrel-shaped region, followed by a second concave barrel-shaped region, followed by an exit region 158.

Dimensional Interrelationships

FIGS. 6-10 show various views of the assembled screw of various embodiments.

Pass-Through

The dimensions of the various components may be such that screw head 250 may, by itself, pass through receiver central hole 110 in receiver 100. The dimensions may be such that when collet 400 is in position around head 250, that combination of collet 400 and screw head 250 cannot pass through receiver central hole 110 in receiver 100. The various dimensions may be such that collet 400 may pass through entry region 152, with some squeezing of collet 400 if necessary.

Gripping of Screw Head

The radius of the internal concave surface 470 of collet 400 may be approximately equal to the spherical radius of the head 250 of screw 200. Thus, collet 400 may be able to easily accept screw head 250 inside it. In order for screw head 250 to go inside collet 400, it may be necessary for collet 400 to spring somewhat further open and then to spring back after screw head 250 is inside collet 400. Thereupon, collet 400 may remain in spring contact with screw head 250, which may help to provide frictional restraint against rotation of screw head 250 with respect to collet 400.

Capturing

Collet 400, screw head 250 and cavity 150 in receiver 100 may be dimensioned such that collet 400 is able to be squeezed suitably to enter through entry region 152, and then is able to expand after having been squeezed, so as to be retained in the configuration in which the collet exerts some frictional restraint against pivoting or rotation of screw head 250. The various dimensions may be such that when collet 400 is inserted into cavity 150 to that appropriate position, the flat surface 430 of collet 400 is in the diverging region 154. As a result, in this situation, collet 400 with screw head 250 inside it is retained inside cavity 150 and cannot easily be removed. The various dimensions may be such that when collet 400 is at a certain position within cavity 150, screw head 250 may be inserted into collet 400 from below. Alternative possibilities include that receiver 100 may comprise a groove suitable for lip 440 to at least partially fit into when collet 400 is inserted sufficiently far into cavity 150. Lip 440 may follow the wall of cavity 150 as collet 400 advances into cavity 150. FIGS. 9 and 10 show the positions of the screw head 250, collet 400 and receiver 100 in two different situations: FIGS. 8 and 9 show the situation where the assembly is untightened and collet 400 exerts moderate frictional force against screw head 250 to maintain a desired position of screw head 250. However, it also is still possible to reposition screw head 250 by exerting a moderate amount of force or torque. FIG. 10 shows the assembly in its final locked situation in which a spinal rod would be at or near the bottom of the U-shaped channel in receiver 100.

Clamping Upon Tightening

At least the lower part of converging region 156 may have a converging region 156 such that at least some of converging region 156 cooperates with a corresponding region of collet 400 to generate wedging force against collet 400 as collet 400 is pushed into converging region 156. The converging region 156 may be converging in the sense of a frustoconical surface having a linear taper, or it may be a curved axisymmetric surface having a nonlinear taper. Similarly, the external surface of collet 400 may be a frustoconical surface having a linear taper, or may be a curved axisymmetric surface having a nonlinear taper. The internal surface of converging region 156 and the external surface of collet 400 may be similar to each other and might be identical to each other but they do not have to be identical. The wedging force exerted on the collet and in turn on the screw head may immobilize screw head 250 due at least in part to the friction resulting from the corresponding force exerted on screw head 250 by collet 400. This situation may occur when a spinal rod is urged against surface 430 of collet 400 by a setscrew engaging threads 170 in receiver 100. Alternatively (not shown), it would also be possible to include an intermediate part between spinal rod 800 and surface 430.

Friction During Handling Prior to Tightening

A further possible feature concerns the "un-locked" situation in which collet 400, containing within it screw head 250, is inserted sufficiently far into cavity 150 so that flat surface 430 is within the diverging region 154. In this "un-locked" situation, collet 400 may be at least slightly deformed from its natural shape and dimensions. This is illustrated in FIG. 8. More specifically, in this situation the sides of collet 400 may be at least slightly bent so that they exert some force on screw head 250. This may cause some friction involving screw head 250 so that in this situation, without a spinal rod or setscrew being in place, the screw 200 may be angulated to any desired angular position relative to receiver 100, within the range of normally permitted positions, and will be held in that position by a modest amount of frictional force due to the side of collet 400 bearing against screw head 250. In this situation, in a cross-section in a plane that passes through the central axis of the screw, there may be contact between the collet and other components at several places. At an end of collet 400 that is farthest from screw shaft 260 (that would appear as an upper portion of the collet 400 in the orientation shown), there may be contact between the exterior of the collet 400 and the cavity 150 at upper external contact point 510. Proceeding away from upper external contact point 510, there may be a non-contact region 520 in which there is not contact between the collet (400) and the cavity (150). Proceeding still further (that would appear as a lower portion of the collet 400 in the orientation shown), there may also be a lower external touching point 530 at which there is again contact between the exterior of the collet 400 and the cavity 150. Somewhere in a middle region of the collet 400, the interior of the collet 400 may contact the screw head 250 at an interior contact point 540. Taken together, these three locations of contact 510, 530, 540 may act as or may approximate a three-point bending situation that deforms collet 400 from its natural configuration and helps to create the described frictional force to maintain screw head 250 in a desired orientation prior to locking.

Action of the Spinal Rod for Locking

It is not necessary that spinal rod 800 actually press on the screw head 250 in the completed assembly. The spinal rod may press on surface 430 of collet 400 and may be fully capable of locking the entire assembly by such action. If the spinal rod 800 presses on the screw head 250 and if screw 200 contains a central hole 280, it is possible that the spinal rod may press on screw head 250 for some angular positions of shaft 260 and not for other angular positions, due to the presence and variable location of central hole 280 through a portion of the screw head 250.

Assemblies, Kit

Assemblies are shown in FIGS. 6-10. The assembly may be assembled by first inserting collet 400 into cavity 150 through entrance region 152, and then screw head 250 may be inserted into the interior of collet 150 through the bottom of receiver 100.

FIGS. 8 and 9 show an assembly in the condition where the relative positions may be adjusted, and FIG. 10 shows the assembly when the parts have been locked. The position of collet 400 in FIG. 10 is visibly different from its position in FIGS. 8 and 9, because in FIG. 10 the collet 400 is lower relative to the receiver 100. Also, as can be seen in FIG. 10, which shows the locked configuration of the assembly, there is a slight gap between the corner of the lip 440 of collet 400, and the nearby interior surface of receiver 100.

Referring now to FIG. 11, there is shown yet another design having many of the already-described features but without the ability to be assembled from the bottom. In this design, screw head 250 may be unable to pass through the bottom of receiver 100. Instead, collet 400 may be inserted through the top of receiver 100 and then screw 200 may be passed through from the top, until screw head 250 is inside collet 400. In this design also, the collet wall may experience a three-point bending situation similar to that discussed in connection with FIG. 8.

All components and tools may be sterile and may be contained in an apparatus suitable to allow sterilization to be performed, or if desired may be packaged appropriately to maintain sterility.

In the case of a cannulated screw, a kit may further include a flowable substance and means for injecting the flowable substance into the central hole 280 in screw 200. The flowable substance may include cement (polymeric based or ceramic based or any other variety) or a bone growth inducing substance such as Bone Morphogenetic Protein, or an osteoconductive substance, or a bone putty, or any combination thereof. The means for injecting may include a syringe or similar device. It is also possible to inject a dye for radiography.

In some embodiments, it is further possible that there may be cross-holes 290 that intersect longitudinal hole 280. This is illustrated in FIG. 12. Such cross-holes 290 may meet the exterior surface of screw 200 at or near the root of thread 270. Such cross-holes 290 may be located toward the distal end of screw 200 and may be distributed at approximately equal angular intervals along the path of the helical thread 270. Cross-holes 290 may be of a diameter appropriate for a flowable substance to flow through the cross-holes. In designs that contain cross-holes 290, longitudinal hole 280 may be a blind hole having a closed end at the distal end of screw 200, as illustrated in FIG. 12. Alternatively, longitudinal hole 280 might be a through-hole having uniform diameter throughout the length of shaft 260, or might have a reduced diameter close to the distal end of screw 200. It is also possible that longitudinal hole 280 might be tapered.

Directional terminology is illustrated in FIGS. 13 and 14. The longitudinal axis 210 of screw 200 is substantially the axis of shaft 260, and longitudinal hole 280 may coincide with longitudinal axis 210. A radial vector is perpendicular to the longitudinal axis 210. A circumferential direction is perpendicular to both of these while not passing through longitudinal axis 210, in a manner typically used for a polar coordinate system. The axis 292 of a cross-hole 290 would be the axis of an imaginary cylinder that envelopes or matches most of the internal surface of the cross-hole 290. For a cross-hole 290 that is drilled, this would also be the rotational axis of a drill used to drill the hole.

One possibility is that the axis 292 of cross-hole 290 may be oriented in a substantially radial direction with respect to the longitudinal axis 210 of screw 200 (i.e., intersecting longitudinal axis 210 perpendicularly, or i.e., intersecting longitudinal axis 210 and lying in a plane that is perpendicular to longitudinal axis 210). This is illustrated in FIG. 12 for a cross-sectional plane that contains longitudinal axis 210. This is also illustrated in FIG. 13 using a cross-section taken perpendicular to longitudinal axis 210. In FIG. 13 the sectioned screw 200 is shown both in a three-dimensional view and in a straight-on cross-sectional view.

It is further possible that at least some of cross-holes 290 do not have to be oriented in a perfectly radial direction as was illustrated in FIGS. 12 and 13. FIG. 14 illustrates a cross-hole 290 that is oriented so that its direction has a circumferential component. It is possible that the orientation of the cross-hole axis 292 might be angled away from the radial direction, and might have a component that is circumferential with respect to the overall axes of screw 200. The axis 292 of cross-hole 290 might lie in one of the infinitely many planes that are perpendicular to longitudinal axis 210, while being oriented such that the cross-hole axis 292 is not actually radial. The orientation of cross-hole axis 292 might be such that cross-hole axis 292 does not intersect longitudinal axis 210.

The orientation of a cross-hole axis 292 of a non-radial cross-hole may be either forward-facing or backward-facing with respect to the radial vector of the screw 200 and with respect to the direction of rotation that would cause advancement of screw 200 into the material that it may be screwed into. A backward-facing orientation is what is illustrated in FIG. 14. In this orientation, as bone material approaches the edge of cross-hole 290 as screw thread 270 advances, the bone material will see an obtuse angle and will somewhat pass over the somewhat hidden acute angle. Thus, a backward-facing orientation of cross-hole 290 may help to reduce the tendency of the edge of the cross-hole 290 to shave bone material as the screw 200 rotates and advances into the bone. This may increase the likelihood of the cross-hole 290 remaining unclogged by bone material and being able to deliver flowable material to the bone when desired.

As described elsewhere herein, external thread 270 may have a path that is generally helical. Yet another possible orientation is that the direction of cross-hole 290 might be oriented such that whatever non-radial component cross-hole axis 292 has substantially aligns with the local helical path of thread 270. Such a cross-hole orientation may be thought of as first of all having a circumferential component, as was illustrated in FIG. 13, and additionally having an axial component chosen so that the circumferential component and the axial component combine to provide a resultant that aligns with the local helical thread pitch angle. For threads having a typical thread pitch, the axial component of that orientation would be significantly smaller than the circumferential component.

As a still more general possibility, it is possible that cross-hole 290 may have a cross-hole axis 292 that has a circumferential component and an axial component; however, the axial component might be of any magnitude so as to create any cross-hole axis orientation that may be desired. The axial component need not be such as to create a cross-hole axis that matches the helical pitch of the helical thread 270 as previously described.

It is further possible that cross-hole 290 might have a smoothed edge at least some of the place where cross-hole 290 meets an external surface of screw 200, such as a countersink or radius or chamfer where the cross-hole 290 meets the thread 270. This may further help to avoid cutting into bone material and generating possibly clogging shavings of bone material. Even further, it is possible that the path of cross-hole 290 may be curved, such as might be manufactured by electrical discharge machining of the screw material. It is also possible that cross-hole 290 may have a cross-sectional shape that is other than circular.

The features illustrated in FIGS. 13 and 14 may be used with polyaxial screws as discussed herein, but in general they may also be used with any type of screw or threaded device intended for medical use such as with bone or other hard tissue. For example, a screw having these features might be a monoaxial pedicle screw, or might be a screw for securing a bone plate, or in general may be a screw for securing any orthopedic device, or it may be an externally threaded delivery device for delivering fluid to bone.

Longitudinal hole 280 may be a through-hole, a blind hole, a hole that is of constant-diameter or tapered or a hole of stepped or variable diameter having any desired relation between respective diameters of respective portions of hole. Holes 290 may, for example, be confined or may be concentrated in the distal portion of screw 200, such as the distal one-third of the length of screw 200. Holes 290 may be sized to be as small as possible in diameter, consistent with achieving sufficient flow of liquid such as resin or dye through holes 290. For example, holes 290 may have a diameter of approximately 0.64 mm (0.025 inch). Such hole diameter also may be appropriate so that possible pillars of hardened resin originating from the holes 290 upon completion of surgery may be broken without requiring extreme amounts of torque, if there is need for removal of the screw 200 during a subsequent revision surgery.

Referring now to FIG. 15, there is shown an injector tube for use in injecting a fluid such as resin or dye into the central hole 280 of a cannulated screw 200 or a cannulated and fenestrated screw 200. The injector tube might further be connected to a hand-operated syringe (not illustrated) or any other appropriate source of the fluid. The injector tube may have an end that fits inside hole 280 in screw 200 loosely enough to permit easy connection but tightly enough to minimize leakage of the supplied fluid through the tube-hole interface. Alternatively, or in addition, a seal feature such as a resilient material may be provided.

Any holes may comprise entry features such as chamfers or rounded edges.

Among other things, some embodiments may provide friction in the un-locked state using a minimum of parts, in fact, using fewer parts than are used for some known designs, or using a number of parts similar to what would be used for a typical non-frictional design.

All referenced documents are incorporated by reference herein. Features described herein may be combined in any combination. Although the invention has been described herein, it is desired that the scope be limited only by the scope of the following claims.

We claim:

1. A polyaxial screw assembly, comprising:
a screw comprising a screw head that is bulbous and a screw shaft having external threads;
a receiver pivotable with respect to said screw head; and
a collet interposed between said screw head and said receiver, said collet having an upper end and a lower end opposed to said upper end;
wherein said polyaxial screw assembly is capable of existing in a non-locked condition,
wherein in said non-locked condition, a first radially-inwardly-facing surface of said receiver exerts a first force on said collet at an upper external touching point at said upper end of said collet; and
wherein a second radially-inwardly-facing surface of said receiver exerts a second force on said collet at a lower external touching point on said collet adjacent said lower end of said collet; and
wherein between said upper external touching point and said lower external touching point there is a non-contact region in which there is no contact between an exterior of said collet and said receiver; and
wherein an outwardly-facing surface of said screw head exerts a third force on said collet at an interior contact point located on an interior of said collet between said upper external touching point and said lower external touching point.

2. A polyaxial screw assembly, comprising:
a screw comprising a screw head that is bulbous and a screw shaft having external threads;
a receiver pivotable with respect to said screw head, having a distal end having a cavity for containing said screw head and having a proximal end opposed to said distal end, having an axial opening through both said proximal end and said distal end; and
a collet interposed between said screw head and said cavity, wherein said collet comprises a proximal upper end and an opposite distal lower end, and a proximal external radially-extending lip at said proximal upper end, and wherein said collet comprises a first plurality of slots extending from said proximal upper end toward said distal lower end, and a second plurality of slots extending from said distal lower end toward said proximal upper end;
wherein said collet can occupy a first condition, in which said screw is frictionally movable with respect to said receiver, and in which a first load is applied to said proximal external radially-extending lip of said collet by a first radially-inward-facing surface of said receiver; and
wherein said collet can occupy a second condition, different from said first condition, in which said screw is immovable with respect to said receiver, and in which a second load is applied to said distal lower end of said collet by a second radially-inward-facing surface of said receiver to urge said collet against said screw head.

3. The polyaxial screw assembly of claim 2, wherein said screw head has a maximum diameter larger than a maximum diameter of said screw shaft.

4. The polyaxial screw assembly of claim 2, wherein said screw head has a maximum diameter larger than a maximum diameter of said external threads.

5. The polyaxial screw assembly of claim 2, wherein said collet comprises a two-dimensionally curved collet exterior surface or surface envelope.

6. The polyaxial screw assembly of claim 2, wherein in said second condition there is no contact between said proximal external radially-extending lip of said collet and said first and second radially-inward-facing surfaces of said receiver.

* * * * *